(12) United States Patent  (10) Patent No.: US 7,517,320 B2
Wibowo et al.  (45) Date of Patent: Apr. 14, 2009

(54) AIRWAY BYPASS SITE SELECTION AND TREATMENT PLANNING

(75) Inventors: Henky Wibowo, Cupertino, CA (US); Edmund J. Roschak, Mission Viejo, CA (US); Thomas M. Keast, Sunnyvale, CA (US); Cary Cole, Mountain View, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 11/772,807

(22) Filed: Jul. 2, 2007

(65) Prior Publication Data

US 2008/0009760 A1  Jan. 10, 2008

Related U.S. Application Data

(60) Provisional application No. 60/825,518, filed on Sep. 13, 2006, provisional application No. 60/822,884, filed on Aug. 18, 2006, provisional application No. 60/806,397, filed on Jun. 30, 2006.

(51) Int. Cl.
*A61B 5/08* (2006.01)
(52) U.S. Cl. ..................................................... 600/529
(58) Field of Classification Search .......... 600/529–543
See application file for complete search history.

(56) References Cited

U.S. PATENT DOCUMENTS 4,930,525 A  6/1990 Palestrant
5,155,435 A  10/1992 Kaufman et al.
5,638,819 A  6/1997 Manwaring et al.
5,782,762 A  7/1998 Vining
5,971,767 A  10/1999 Kaufman et al.
6,083,162 A  7/2000 Vining
6,181,348 B1  1/2001 Geiger
6,188,355 B1  2/2001 Gilboa
6,226,543 B1  5/2001 Gilboa et al.
6,246,784 B1  6/2001 Summers et al.
6,272,366 B1  8/2001 Vining
6,331,116 B1  12/2001 Kaufman et al.
6,343,936 B1  2/2002 Kaufman et al.
6,346,940 B1  2/2002 Fukunaga
6,380,732 B1  4/2002 Gilboa
6,409,686 B1  6/2002 Guthrie et al.

(Continued)

FOREIGN PATENT DOCUMENTS

WO  WO0601731 A2  2/2006
WO  WO06014732 A2  2/2006

OTHER PUBLICATIONS

A. Misra, M. Rudrapatna, A. Sowmya, "Automatic Lung Segmentation: A Comparison of Anatomical and Machine Learning Approaches" proceedings of International Conference on Intelligent Sensors, Sensor Networks and Information Processing, 451-456, 2004.*

(Continued)

*Primary Examiner*—Robert L Nasser
*Assistant Examiner*—Karen E Toth
(74) *Attorney, Agent, or Firm*—Levine Bagade Han LLP

(57) ABSTRACT

The invention relates to systems and methods for site selection and placement of extra-anatomic passages altering gaseous flow in a diseased lung.

44 Claims, 11 Drawing Sheets

U.S. PATENT DOCUMENTS

| | | | |
|---|---|---|---|
| 6,466,687 B1 | 10/2002 | Uppaluri et al. | |
| 6,505,065 B1 | 1/2003 | Yanof et al. | |
| 6,556,696 B1 | 4/2003 | Summers et al. | |
| 6,558,333 B2 | 5/2003 | Gilboa et al. | |
| 6,574,498 B1 | 6/2003 | Gilboa | |
| 6,593,884 B1 | 7/2003 | Gilboa et al. | |
| 6,615,155 B2 | 9/2003 | Gilboa | |
| 6,692,494 B1 | 2/2004 | Cooper et al. | |
| 6,694,163 B1 | 2/2004 | Vining | |
| 6,702,780 B1 | 3/2004 | Gilboa et al. | |
| 6,711,429 B1 | 3/2004 | Gilboa et al. | |
| 6,712,812 B2 | 3/2004 | Roschak et al. | |
| 6,749,606 B2 | 6/2004 | Keast et al. | |
| 6,785,410 B2 | 8/2004 | Vining et al. | |
| 6,819,785 B1 | 11/2004 | Vining et al. | |
| 6,829,379 B1 | 12/2004 | Knoplioch et al. | |
| 6,833,814 B2 | 12/2004 | Gilboa et al. | |
| 6,909,913 B2 | 6/2005 | Vining | |
| 6,996,430 B1 | 2/2006 | Gilboa et al. | |
| 7,149,564 B2 | 12/2006 | Vining et al. | |
| 7,175,644 B2 | 2/2007 | Cooper et al. | |
| 7,179,220 B2 | 2/2007 | Kukuk | |
| 7,191,101 B2 | 3/2007 | Knoplioch et al. | |
| 7,232,409 B2 | 6/2007 | Hale et al. | |
| 7,236,620 B1 | 6/2007 | Gurcan | |
| 7,260,250 B2 | 8/2007 | Summers et al. | |
| 7,356,367 B2 | 4/2008 | Liang et al. | |
| 2001/0044576 A1 | 11/2001 | Vining | |
| 2002/0028006 A1* | 3/2002 | Novak et al. | 382/128 |
| 2002/0028008 A1* | 3/2002 | Fan et al. | 382/131 |
| 2002/0131625 A1 | 9/2002 | Vining et al. | |
| 2002/0133057 A1 | 9/2002 | Kukuk | |
| 2003/0070676 A1 | 4/2003 | Cooper et al. | |
| 2004/0073155 A1 | 4/2004 | Laufer et al. | |
| 2005/0016530 A1* | 1/2005 | McCutcheon et al. | 128/200.24 |
| 2005/0043751 A1 | 2/2005 | Phan et al. | |
| 2005/0043752 A1 | 2/2005 | Phan et al. | |
| 2005/0060041 A1 | 3/2005 | Phan et al. | |
| 2005/0060042 A1 | 3/2005 | Phan et al. | |
| 2005/0060044 A1 | 3/2005 | Roschak et al. | |
| 2005/0135662 A1 | 6/2005 | Vining et al. | |
| 2005/0137518 A1 | 6/2005 | Biggs et al. | |
| 2005/0137611 A1 | 6/2005 | Escudero et al. | |
| 2005/0137715 A1 | 6/2005 | Phan et al. | |
| 2005/0147284 A1 | 7/2005 | Vining et al. | |
| 2005/0177144 A1 | 8/2005 | Phan et al. | |
| 2005/0182295 A1 | 8/2005 | Soper et al. | |
| 2005/0261550 A1 | 11/2005 | Akimoto et al. | |
| 2006/0023966 A1 | 2/2006 | Vining | |
| 2007/0092864 A1* | 4/2007 | Reinhardt et al. | 435/4 |

OTHER PUBLICATIONS

Coxson, H. et al., "A Quantification of the Lung Surface Area in Emphysema Using Computed Tomography," *AM J Respir Crit Care Md* 159:851-856, 1999.

Coxson, H. et al., "Measurement of Lung Expansion with Computed Tomography and Comparison withQuantitive Histology," *J. Appl Physiol*, 79(5); 1525-1530, 1995.

Gevenois, P., et al. "Pulmonary Emphysema: Quantitative CT During Expiration," *Radiology* 199;825-829, 1996.

Hoffman, E., et al., "A Structural and Functional Assessment of the Lung via Multidetector-Row Computed Tomography Phenotyping Chronic Obstructive Pulmonary Disease," *Proc Am Thorac Soc*, 3:519-534, 2006.

Kuhnigk, J-M, et al., "New Tools for Computer Assistance in Thoracic CT Part 1. Functional Analysis of Lungs, Lung Lobes, and Bronchopulmonary Segments", *RadioGraphics* 25:525-536, 2005.

Madani, A., et al., "Objective Quantification at Multi-Detector Row CT - Comparison with Macroscopic and Microscopic Morphometry", *Radiology*: 238(3): 1036-1043, 2006.

Madani, A., et al., "Quantitative Computed Tomography Assessment of Lung Structure and Function in Pulmonary Emphysema," *Eur Respir J*, 18: 720-730, 2001.

Nakano Y., et al., "Computed Tomographic Measurements of Airway Dimensions and Emphysema in Smokers Correlation with Lung Function," *Am J Respir Crit Care Med* 162: 1102-1108, 2000.

Newell, J.D., et al., Report of a Workshop: Quantitative Computed Tomography Scanning in Longitudinal Studies of Emphysema, *Eur Respir J*, 23: 769-775, 2004.

Tschirren, J., et al. "Segmentation and Quantitative Analysis of Intrathoracic Airway Trees from Computed Tomography Images," *Proc Am Thorac Soc*, 2:484-487, 2005.

Zaporozhan, J. et al. "Multi-Detector CT of the Chest: Influence of Dose Onto Quantitative Evaluation of Severe Emphysema A Simulation Study." *J Comput Assist Tomogr* 30:460-468, 2006.

* cited by examiner

| Lobe | Right Upper | | | Right Lower | | | | |
| --- | --- | --- | --- | --- | --- | --- | --- | --- |
| Airways | $B^1$ | $B^2$ | $B^3$ | $B^6$ | $B^7$ | $B^8$ | $B^9$ | $B^{10}$ |
| Emphysematous Tissue Coalescent Pattern (Severe - 20, Moderate - 10, Mild - 0) | 20 | 20 | 20 | 20 | N/A | N/A | 20 | 20 |
| Proximity to Nearest Region w/Tissue Destruction(mm) | < 5 | < 5 | < 5 | < 5 | N/A | N/A | < 5 | < 5 |
| Clear Access to Nearest Region w/Tissue Destruction(mm) | Clear | Clear | Clear | Clear | N/A | N/A | Clear | Clear |
| Average Diameter (mm) | 6 | 6 | 9 | 6 | N/A | N/A | 5 | 7 |
| Distance from the Carina (mm) | 66 | 56 | 53 | 76 | N/A | N/A | 96 | 90 |
| Avg. Airway Thickness (mm) | 2.1 | 1.1 | 1.3 | 1.3 | N/A | N/A | 2.1 | 1.2 |
| Grade | 100 | 100 | 100 | 100 | 0 | 0 | 90 | 100 |

FIG. 2D

| Lobe | Left Upper | | | | Left Lower | | | |
| --- | --- | --- | --- | --- | --- | --- | --- | --- |
| Airways | $B^{1+2}$ | $B^3$ | $B^4$ | $B^5$ | $B^6$ | $B^{7+8}$ | $B^9$ | $B^{10}$ |
| Emphysematous Tissue Coalescent Pattern (Severe - 20, Moderate - 10, Mild - 0) | 20 | 20 | 20 | 20 | 20 | 20 | 20 | 20 |
| Proximity to Nearest Region w/Tissue Destruction(mm) | < 5 | < 5 | < 5 | < 5 | < 5 | < 5 | < 5 | < 5 |
| Clear Access to Nearest Region w/Tissue Destruction(mm) | Clear | Clear | Clear | Clear | Clear | Clear | Clear | Clear |
| Average Diameter (mm) | 5 | 7 | 6 | 5 | 8 | 7 | 7 | 7 |
| Distance from the Carina (mm) | 103 | 91 | 92 | 92 | 84 | 102 | 105 | 93 |
| Avg. Airway Thickness (mm) | 1.3 | 1.2 | 1.1 | 1.2 | 1.4 | 1.3 | 1.5 | 3.2 |
| Grade | 90 | 100 | 100 | 90 | 100 | 100 | 100 | 100 |

FIG. 2E

| LOBES | SEGMENTAL AIRWAY | RADIOLOGIST'S NOTES | GRADE |
|---|---|---|---|
| Right Upper | $B^1$ Apical | Recommended Location: Tricky-about halfway to the first branching of the segment. Access Direction: Lateral and slightly posterior on axial and coronal views. Emphysema Rating: Moderate to severe. Blood Vessels: Narrow window between a vessel straight lateral and a smaller one posterolateral on axial. | 100 |
| Right Upper | $B^2$ Posterior | Recommended Location: Just before the branching of this short segmental bronchus. Access Direction: Lateral and anterior on axial view; lateral and slightly inferior on coronal. Alternatively, posterior and medial on axial, also posterior on sagittal. Emphysema Rating: Severe. Blood Vessels: Large vessels anterior and medial; moderate vessel on sagittal is seen at a slight distance posteriorly. | 100 |
| Right Upper | $B^3$ Anterior | Recommended Location: Before the apical segment arises from the bronchus. Access Direction: Lateral on axial and coronal views. Emphysema Rating: Severe. Blood Vessels: Small vessels in bronchial wall, seen as bulges on coronal superior and inferolateral, as well as further anterior and posterior to the location on axial. | 100 |
| Right Middle | $B^4$ Lateral | Recommended Location: Before first branching of segment. Access Direction: On coronal view, note good access inferiorly, also seen on sagittal. Emphysema Rating: Moderate to severe. Blood Vessels: Vessels anterior, posterior, medial. Only short distance to large vessel superiorly. | N/A |
| Right Middle | $B^5$ Medial | Recommended Location: Just before branching of this segment. Access Direction: Inferiorly on coronal and sagittal. Also posterolateral on axial. Emphysema Rating: Severe. Blood Vessels: Not much clearance beyond bronchus posteriorly; Other branch and vessel anteriorly. | N/A |
| Right Lower | $B^6$ Superior | Recommended Location: Just before the division of this short bronchus. Access Direction: Either medial or lateral on coronal view and medially on axial view. Emphysema Rating: Severe. Blood Vessels: Vessels thicken the lateral wall of the bronchus proximally unless one goes through the lateral wall of the lateral branch at its origin. | 100 |
| Right Lower | $B^7$ Medial Basal | Bronchus is too small to analyze. | 0 |
| Right Lower | $B^8$ Anterior | Bronchus is too small to analyze. | 0 |
| Right Lower | $B^9$ Lateral Basal | Recommended Location: Narrow bronchus, but before first branch. Access Direction: Anterior on axial and sagittal views. Emphysema Rating: Severe. Blood Vessels: Probably incomplete fissure, with this approach into the middle lobe. Blood vessels are observed in all other directions. | 90 |
| Right Lower | $B^{10}$ Posterior Basal | Recommended Location: Before first branch, about 1cm. Access Direction: Clear medially on axial and coronal. Emphysema Rating: Severe. Blood Vessels: Lots of vessels lateral and branches and vessels anteriorly. | 100 |

FIG. 2F

| LOBES | SEGMENTAL AIRWAY | RADIOLOGIST'S NOTES | GRADE |
|---|---|---|---|
| Left Upper | $B^{1+2}$ Apicoposterior | Recommended Location: Before a tiny lateral branch takes off.<br>Access Direction: Good access laterally on axial and coronal, as well as posteriorly on axial and sagittal.<br>Emphysema Rating: Severe.<br>Blood Vessels: Bronchus still fairly thick at this point. | 90 |
| Left Upper | $B^3$ Anterior | Recommended Location: Quite proximal, before a lateral branch takes off.<br>Access Direction: Laterally on axial and coronal.<br>Emphysema Rating: Severe.<br>Blood Vessels: Blood vessels are observed medially and superiorly. | 100 |
| Left Upper | $B^4$ Superior | Recommended Location: Shortly after the lingula bifurcates.<br>Access Direction: Anteromedially on axial view; superoanteriorly on sagittal view.<br>Emphysema Rating: Moderate to severe.<br>Blood Vessels: Vessel's lateral, posterior, and inferior. | 100 |
| Left Upper | $B^5$ Inferior | Recommended Location: Prior to branching as bronchus widens.<br>Access Direction: Good anterior access on axial, although sagittal suggests that the direction is critical.<br>Emphysema Rating: Severe.<br>Blood Vessels: Vessels supero- and infero-laterally on sagittal view; laterally on axial and coronial views. | 90 |
| Left Lower | $B^6$ Superior | Recommended Location: A short distance before the first division of this short bronchus.<br>Access Direction: Posteromedially on axial view; inferomedial on coronal.<br>Emphysema Rating: Severe.<br>Blood Vessels: Fairly thick bronchial wall; probably thickened by vessel inferolaterally. | 100 |
| Left Lower | $B^{7+8}$ Anteromedial | Recommended Location: Good-sized segmental bronchus.<br>Access Direction: Anterior on axial and sagittal views.<br>Emphysema Rating: Severe.<br>Blood Vessels: Large vessel lateral; other bronchi and vessels posterior. | 100 |
| Left Lower | $B^9$ Lateral | Recommended Location: Beyond the trifurcation and before the next branch.<br>Access Direction: Posterolaterally on axial, laterally on coronal and posteriorly on sagittal.<br>Emphysema Rating: Moderate to severe.<br>Blood Vessel: Vessels and bronchi anterior and medial. | 100 |
| Left Lower | $B^{10}$ Posterior Basal | Recommended Location: Follow the segment to just before it branches posterosuperiorly.<br>Access Direction: On axial and coronal, either medial or lateral; prefer lateral for worse disease.<br>Emphysema Rating: Moderate to severe.<br>Blood Vessels: Vessels posterior and anterior on axial. | 100 |

FIG. 2G

AIRWAY BYPASS SITE SELECTION AND TREATMENT PLANNING

FIELD OF THE INVENTION

The invention relates to methods and systems to select sites within the lungs that allow expired air to pass out of the lung tissue to facilitate both the exchange of oxygen ultimately into the blood and/or to decompress hyper-inflated lungs.

BACKGROUND OF THE INVENTION

The American Lung Association (ALA) estimates that nearly 16 million Americans suffer from chronic obstructive pulmonary disease (COPD) which includes diseases such as chronic bronchitis, emphysema, and some types of asthma. The ALA estimated that COPD was the fourth-ranking cause of death in the U.S. The ALA estimates that about 14 million and 2 million Americans suffer from emphysema and chronic bronchitis respectively.

Those inflicted with COPD face disabilities due to the limited pulmonary functions. Usually, individuals afflicted by COPD also face loss in muscle strength and an inability to perform common daily activities. Often those patients desiring treatment for COPD seek a physician at a point where the disease is advanced. Since the damage to the lings is irreversible, there is little hope of recovery. Most times, the physician cannot reverse the effects of the disease but can only offer treatment and advise to halt the progression of the disease.

To understand the detrimental effects of COPD, the workings of the lungs requires a cursory discussion. The primary function of the lungs is to permit the exchange of two gasses by removing carbon dioxide from arterial blood and replacing it with oxygen. Thus, to facilitate this exchange, the lungs provided a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. Specifically, the airway begins with the trachea which branches into the left and right bronchi which divide into lobar, then segmental bronchi. Ultimately, the branching continues down to the terminal bronchioles which lead to the alveoli. Plates of cartilage may be found as part of the walls throughout most of the airway from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles are the smallest airways that do not contain alveoli. The function of the bronchi and bronchioles is to provide conducting airways that lead air to and from the gas-blood interface. However, these conducting airways do not take part in gas exchange because they do not contain alveoli. Rather, the gas exchange takes place in the alveoli which are found in the distal most end of the airways.

The mechanics of breathing include the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric. Consequently, air flows into the lungs and the lungs expand. During unforced expiration, the inspiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed atmospheric pressure causing air to flow out of the lungs and deflate the lungs. If the lungs' ability to recoil is damaged, the lungs cannot contract and reduce in size from their inflated state. As a result, the lungs cannot evacuate all of the inspired air.

In addition to elastic recoil, the lung's elastic fibers also assist in keeping small airways open during the exhalation cycle. This effect is also known as "tethering" of the airways. Tethering is desirable since small airways do not contain cartilage that would otherwise provide structural rigidity for these airways. Without tethering, and in the absence of structural rigidity, the small airways collapse during exhalation and prevent air from exiting thereby trapping air within the lung.

Emphysema is characterized by irreversible biochemical destruction of the alveolar walls that contain the elastic fibers, called elastin, described above. The destruction of the alveolar walls results in a dual problem of reduction of elastic recoil and the loss of tethering of the airways. Unfortunately for the individual suffering from emphysema, these two problems combine to result in extreme hyperinflation (air trapping) of the lung and an inability of the person to exhale. In this situation, the individual will be debilitated since the lungs are unable to perform gas exchange at a satisfactory rate.

One further aspect of alveolar wall destruction is that the airflow between neighboring air sacs, known as collateral ventilation or collateral air flow, is markedly increased as when compared to a healthy lung. While alveolar wall destruction decreases resistance to collateral ventilation, the resulting increased collateral ventilation does not benefit the individual since air is still unable to flow into and out of the lungs. Hence, because this trapped air is rich in $CO_2$, it is of little or no benefit to the individual.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD.

Moreover, patients requiring a supplemental source of oxygen are usually never able to return to functioning without the oxygen.

Lung volume reduction surgery is a procedure which removes portions of the lung that are over-inflated. The portion of the lung that remains has relatively better elastic recoil, providing reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the ling term benefits of this surgery are still being evaluated. In any case, ti is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung which was compressing healthier portions of the lung allows the healthier portions to expand, increasing the overall efficiency of the lung. If the entire lung is emphysematous, however, removal of a portion of the lung removes gas exchanging alveolar surfaces, reducing the overall efficiency of the lung. Lung volume reduction surgery is thus not a practical solution for treatment of emphysema where the entire lung is diseased. Moreover, conventional lung volume reduction surgery is an open surgical procedure which carries the risk of surgical complications and requires a significant period of time of recuperation.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous. The production and maintenance of collateral openings through an airway wall allows air to pass directly out of the lung tissue responsible for gas exchange. These collateral openings serve to decompress hyperinflated lungs and/or facilitate an exchange of oxygen into the blood.

Methods and devices for creating and maintaining collateral channels are discussed in U.S. patent application Ser. No. 09/947,651, filed on Aug. 7, 2000; U.S. patent application Nos. 09/947,144, 09/946,706, and 09/947,126 all filed on Sep. 4, 2001; U.S. Provisional Application No. 60/317,338 filed on Sep. 4, 2001;U.S. Provisional Application No. 60/334,642 filed on Nov. 29, 2001; U.S. Provisional Application No. 60/367,463 filed on Mar. 20, 2002; and U.S. Provisional Application No. 60/374,022 filed on Apr. 19, 2002 each of which is incorporated by reference herein in its entirety.

Benefits in creating these extra-anatomic or collateral channels the lungs of emphysema patients are becoming more readily apparent. However, the degree of benefit of this treatment is believed to be related to the placement of the extra-anatomic passage in a safe manner and in a desired relationship to the area of tissue destruction.

Currently, medical practitioners often perform or rely on external imaging (e.g., via a CT scan) of the diseased lung to estimate a desired area for treatment. Next, the surgeon accesses the airways with a bronchoscope type device to search for vessels using (typically using a Doppler-type device). However, even if the potential area of diseased tissue if located via the external imaging, the surgeon must attempt to navigate the tortuous airways to find an acceptable site for treatment. Often this approach relies on scanning for blood vessels. Such an approach results in lengthy procedure.

In many cases, the surgeon places the patient under anesthesia or a sedative during the procedure. Naturally, a lengthy procedure requires the use of additional drugs or anesthesia to control the patient. In some cases, procedures may be prematurely terminated if the length of the procedure begins to require an excessive amount of anesthesia or sedatives. In addition, the use of the bronchoscope or other access device beyond a certain time may result in additional complications to the patient.

In yet another drawback, the lack of a treatment pan may cause some surgeons to create as many extra-anatomic passages (and implants within the passages) as possible to increase the likelihood that one or more passages is located closely to an area of disease tissue.

In view of the above, there remains a need to improve the site selection and or treatment plan process when performing the procedure. Such an improvement may increase safety by reducing the likelihood of creating the passage in an anatomically undesirable area, improve effectiveness by placing the passage in an area that provides significant benefit, and reduce the procedure time. At the very least, there remains a need for providing physicians with additional information to make informed decisions on possible locations to create extra-anatomic passages for decompressing hyperinflated lungs.

SUMMARY OF THE INVENTION

Previous studies indicate that successful site selection for creation of an extra-anatomic passage includes the ability to gain access to the target airway surface, transbronchial access to trapped gases within the lungs or at least transbronchial access to collateral ventilation paths in the lung, as well as creation of the extra-anatomic passage in an area that is anatomically safe.

For example, the ability to access the target airway surface may be difficult or impossible if the surgical system is unable to navigate to the site. Since the surgical system used to perform the procedure may include any number of components, the component limitations may limit the areas of the airway that are treatable. For example, system components may include devices such as bronchoscopes, guide catheter, hole-maker, implant deployment catheter, etc.

For example, creation of an extra-anatomic passage too close to a blood vessel is obviously not desired. Furthermore, creation of an extra-anatomic passage outside of the parenchymal border of the lung may result in a treatment without benefit or at the worst case, a pneumomediastinum (i.e., free air in the mediastinum that may give rise to pneumothorax or pneumopericardium and compromise the lungs or heart). Alternatively, creating the passage too close to the outer periphery of the lung may result in a pneumothorax.

This invention relates to systems and methods for site selection and placement of extra-anatomic passages altering gaseous flow in a diseased lung.

A method includes assessing a plurality of sites in airways of a hyperinflated lung of a patient by identifying the plurality of site within the airways of the diseased lung, determining at least one anatomic characteristic of each site, assessing a degree of a plurality of diseased regions in the lung, calculating a score for each site based on the degree of the plurality of diseased regions in the lung, at least one anatomic characteristic of each site and a proximity of the site to at least one of the diseased regions, and displaying each score in association with each site in graphical form.

A variation of the inventive method includes the act of selecting a site for creation of an extra-anatomic passage for collateral ventilation of the diseased lung and creating at least one collateral channel or passage at the site. The terms "passage" and/or "channel", are intended to include an opening, cut, slit, tear, puncture, or any other conceivable artificially created opening.

The systems and methods described herein may be incorporated with any number of systems that allow for real-time or virtual mapping through anatomy. In such cases, the methods and systems described herein may be combined with such real-time or virtual mapping systems so as to provide data or other information to the end-user for improved placement and site selection of the extra-anatomic passages.

For example, U.S. Pat. No. 6,466,687, the entirety of which is incorporated by reference, describes method and apparatus for analyzing CT images to determine the presence of pulmonary tissue pathology. The systems of the present invention may be combined with such teachings to identify the tissue pathology as well as provide a treatment plan.

In addition, systems an devices exist for tracking a probe such as a catheter or endoscope through the body of a patient. Such systems and devices are described in U.S. Pat. No. 6,188,355 entitled Wireless six-degree-of-freedom locator; U.S. Pat. No. 6,226,543 entitled System and method of recording and displaying in context of an image a location of at least one point-of-interest in a body during an intra-body medical procedure; U.S. Pat. No. 6,380,732 entitled Six-degree of freedom tracking system having a passive transponder on the object being tracked; U.S. Pat. No. 6,558,333 entitled System and method of recording and displaying in context of an image a location of at least one point-of-interest in a body during an intra-body medical procedure; U.S. Pat. No. 6,574,498 entitled Linking of an intra-body tracking system to external reference coordinates; U.S. Pat. No. 6,593,884 entitled Intrabody navigation system for medical applications; U.S. Pat. No. 6,615,155 entitled Object tracking using a single sensor or a pair of sensors; U.S. Pat. No. 6,702,780 entitled Steering configuration for catheter with rigid distal device; U.S. Pat. No. 6,711,429 entitled System and method for determining the location of a catheter during an intra-body medical procedure; U.S. Pat. No. 6,883,814 entitled Intrabody navigation system for medical applications; and U.S. Pat. No. 6,996,430 entitled Method and system for displaying cross-sectional images of a body. Each of which is incorporated by reference in their entirety. Again, the present invention contemplates combining the systems and methods described above such that the potential treatments sites may be selected and transmitted to the tracking system to assist the medical practitioner in navigating to the sites in an expedited manner.

Methods and devices for creation of the extra-anatomic passage and placement of an implant therein are disclosed in U.S. Pat. No. 6,692,494, and publication Nos.: US-2004-0073155-A1, US-2005-0137518-A1, US-2005-0137712-A1, US-2005-0192526-A1, US-2005-0043752-A1, US-2005-0043751-A1, US-2005-0060042-A1, US-2005-0060041-A1, US-2005-0137611-A1, US-2005137715-A1, US-2005-0060044-A1, US-2005-0177144-A1, PCT/US2005/025738, and PCT/US2005/025739. The entirety of each of which is incorporated by reference.

In another variation, the method and procedures described herein can be performed solely on data and other imaging. For example, a medical practitioner can submit the appropriate scans and other images for analysis by the methods described herein. Accordingly, the analysis and methods described herein can be performed solely on the information provided by the medical practitioner. After the imaging and data are assessed as described below, the medical practitioner will receive ratings or grades of tentative treatment sites (along with the other information discussed below).

BRIEF DESCRIPTION OF THE DRAWINGS

FIGS. 2D-2G show additional displays of information to assist a surgical practitioner in assessing sites within the airways for creation of extra-anatomic paths.

DETAILED DESCRIPTION OF THE INVENTION

Figure 1A:
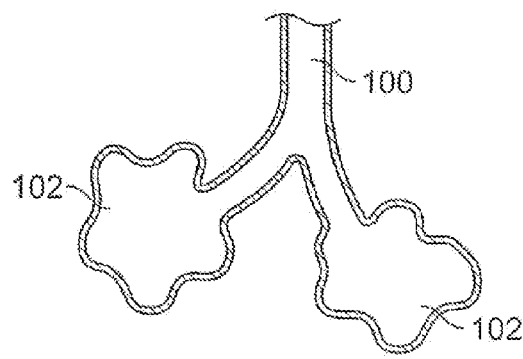
FIGS. 1A-1C illustrate various states of the natural airways and the blood-gas interface.
Figure 1B:
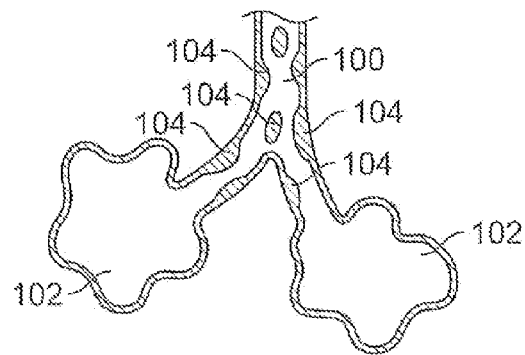
Figure 1C:
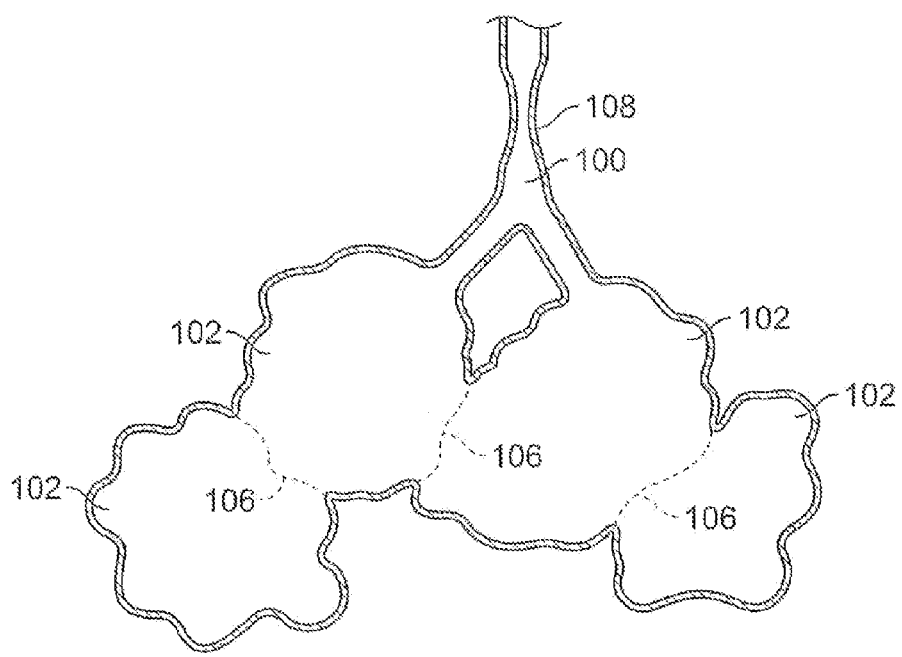

FIG. 1A shows a simplified illustration of a natural airway 100 which eventually branches to a blood gas interface 102. FIG. 1B illustrates an airway 100 and blood gas interface 102 in an individual having COPD. The obstructions 104 (e.g., excessive mucus resulting from COPD, see above) impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. More usually, the states of the lung depicted in FIGS. 1B and 1C are often found in the same lung.

As will be explained in greater detail below, the production and maintenance of collateral openings or channels through airway walls permits expired air to pass directly out of the lung tissue and into the airways to ultimately facilitate exchange of oxygen into the blood and/or decompress hyper inflated lungs. The term 'lung tissue' is intended to include the tissue involved with gas exchange including but not limited to, gas exchange membranes, alveolar walls, parenchyma, airway walls and/or other such tissue. To accomplish the exchange of oxygen, the collateral channels allow fluid communication between an airway and lung tissue. Therefore, gaseous flow is improved within the lung by altering or redirecting the gaseous flow within the lung, or entirely within the lung.

Figure 1D:
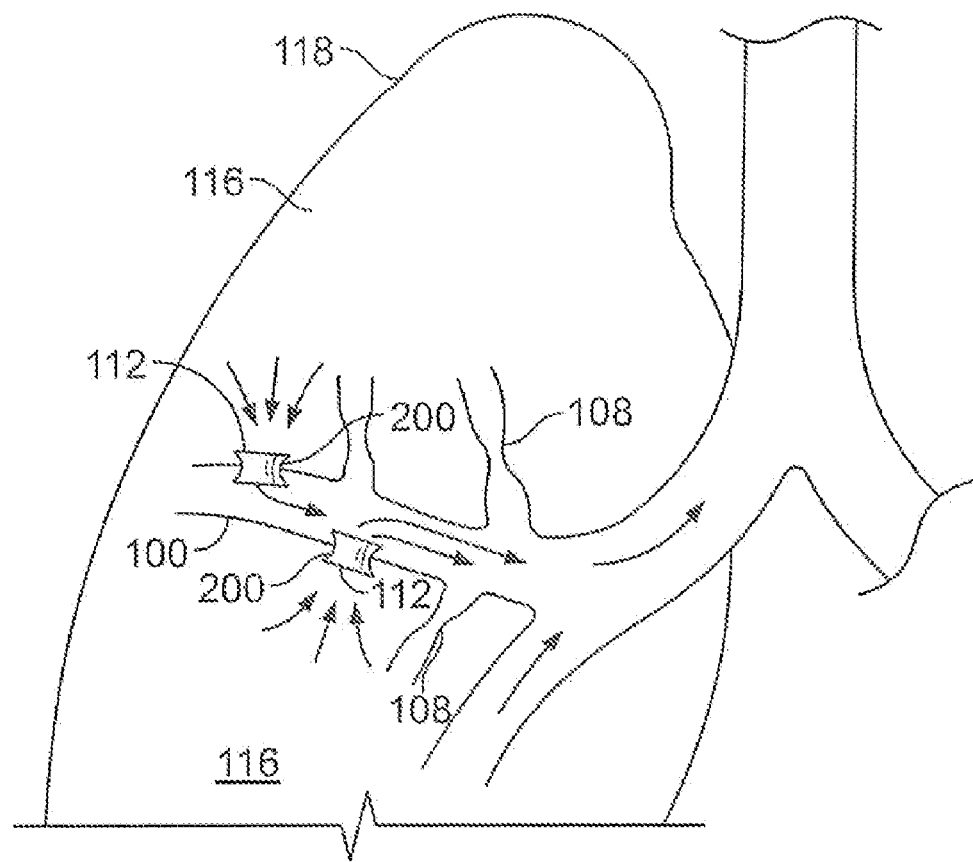
FIG. 1D illustrates a schematic of a lung demonstrating a principle of the effect of collateral channels placed therein.

FIG. 1D illustrates a schematic of a lung 118 to demonstrate a benefit of the production and maintenance of collateral openings or channels through airway walls. As shown, a collateral channel 112 (located in an airway wall 110) places lung tissue 116 in fluid communication with airways 100 allowing expired air to directly pass out of the airways 100. The term channel is intended to include an opening, cut, slit, tear, puncture, or any other conceivable artificially created opening. As shown, constricted airways 108 may ordinarily prevent air from exiting the lung tissue 116. In the example illustrated in FIG. 1D, there is no implanted structure placed in the collateral channel 112. However, conduits or implants 120 may be placed in the collateral channels 112 to assist in maintaining the patency of the collateral channels 112. Examples of conduits may be found in the applications discussed above.

As discussed above, the methods and systems described herein include methods of determining airway bypass stents placements using radiology analysis techniques. Alternatively, the methods and systems described herein can be used merely for the creation of extra-anatomic passages without the placement of stents. Although the analysis may be performed using a computed tomography (CT) scan, the analysis techniques may include the use of non-invasive imaging such as x-ray, ultrasound, Doppler, acoustic, MRI, PET scans or other imaging as well as CT.

In addition, the analysis techniques may include the use of agents delivered within the airways or lungs for improving the imaging. For example, a gas may be inserted into the lungs to provide contrast to identify hyperinflation of the lungs during an x-ray or other non-invasive imaging. For example, 133Xe (Xenon 133) may be used as the agent. Also, a contrast agent may help in identifying blood vessels during CT scans. Another example includes inserting a fluid in the lungs to couple an ultrasound sensor to the wall of an airway.

Figure 2A:
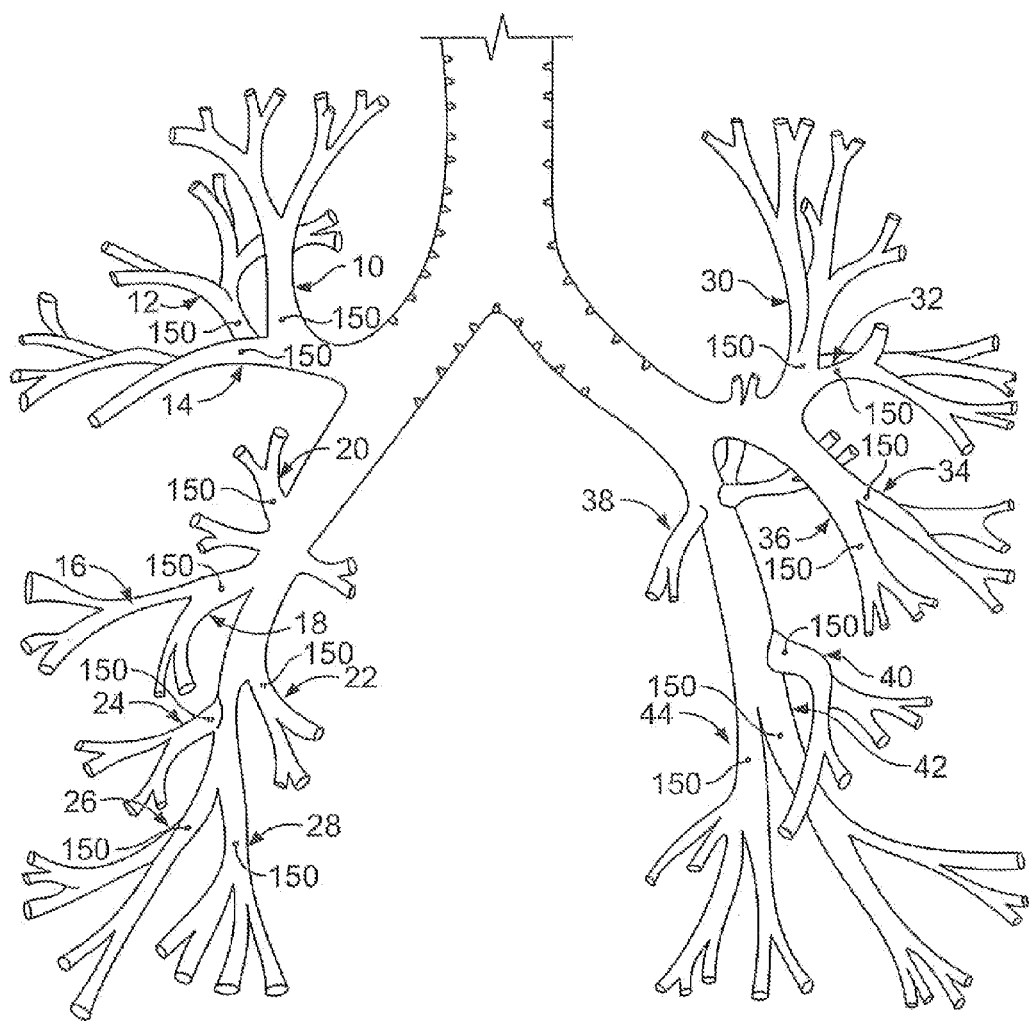
FIG. 2A illustrates an example of sample sites that are identified prior to the method described herein.

As illustrated in FIG. 2A, a number of pre-determined potential sites 150 within the bronchi of the lungs in chosen for analysis. However, any number of site selection modes may be incorporated into the method. For example, a medical practitioner could select a number of areas thought to hold potential benefit upon treatment. In such a case, the practitioner could make the assessment based on imaging, physical examination, or any other means. In the current variation, 18 sites are chosen, in part, based on a medical practitioner's familiarity with the anatomy of the lungs. Using locations that are well known to those familiar with the anatomy of the bronchi reduces the likelihood that the practitioner confuses one site with another. In other words, the pre-selected sites can be identified during the method of assessing the sites and eliminate the practitioner from having to select the sites. Alternatively, pre-selection of sites may occur via one surgical practitioner who then supplies this data to the entity performing the analysis to rate the sites selected by the practitioner.

Accordingly, one variation of the invention includes sleeting sites at major branching points of the bronchi to reduce the likelihood that a medical practitioner mistakes sites. FIG. 2A illustrates these sites as follows: B1—apical upper right lobe 10, B2—posterior upper right lobe 12, B3—anterior upper right lobe 14, B4—lateral middle right lobe 16, B5—medial basal lower right lobe 18, B6—superior lower right lobe 20, B7—medial basal lower right lobe 22, B8—anterior basal lower right lobe 24, B9—lateral basal lower right lobe 26, B10—posterior basal lower right lobe 28, B1+2—apicoposterior upper left lobe 30, B3—anterior upper left lobe 32, B4—superior upper left lobe 34, B5—inferior upper left lobe 36, B6—superior lower left lobe 38, B7+8—anteromedial lower left lobe 40, B9—lateral basal lower left lobe 42, B10—posterior basal lower left lobe 44.

As noted herein, the method is intended to provide a comprehensive analysis to assist a physicians or surgeon in determining which of the pre-selected locations 50 are optimal treatment locations. As a result, although the analysis is performed on any number of given sites to provide a rating or score of the site, the invention does not restrict a medical practitioner from foregoing treatment in nay site for nay number of reasons.

Figure 2B:
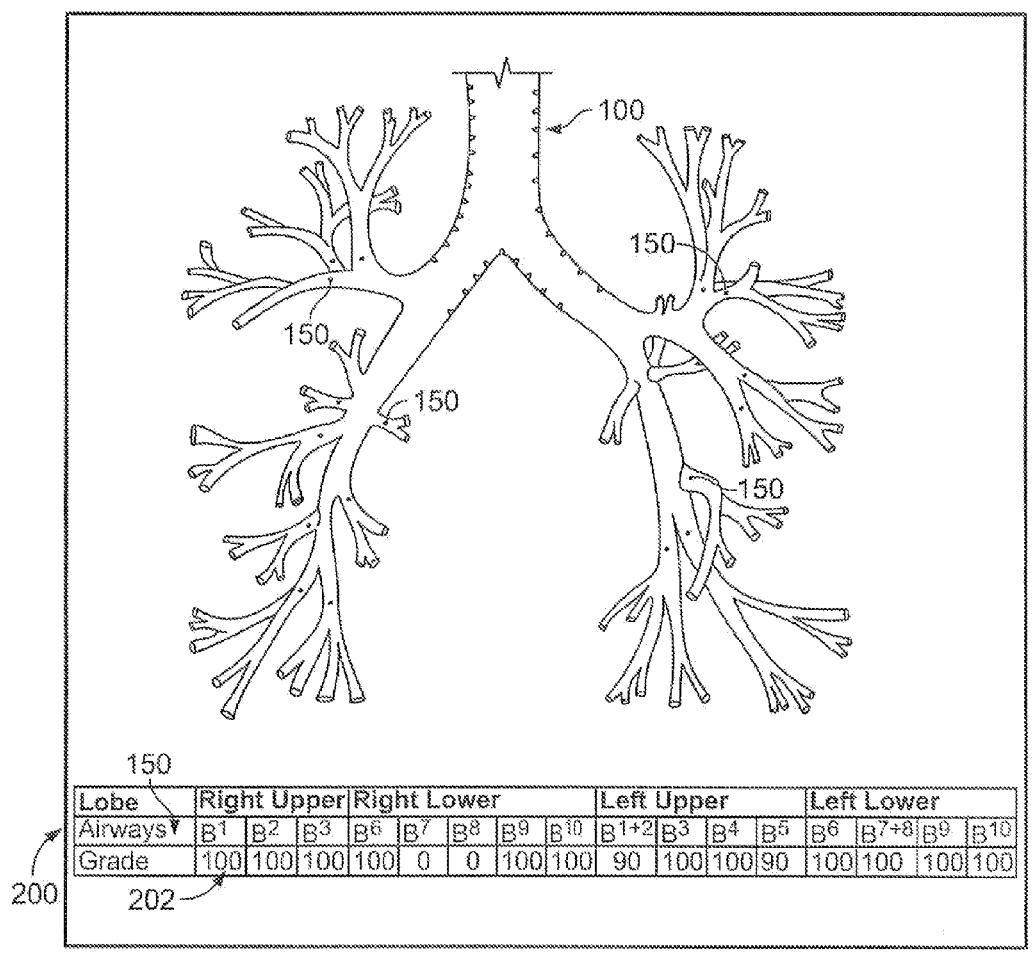
FIG. 2B illustrates an example of a visual display of the results of calculating a score associated with each respective site.

As discussed below, the method includes calculating or assigning a score the sites 50 to provide a quantifiable measure for the practitioner to determine the optimal treatment locations. FIG. 2B shows a sample of such a display 200. As shown, the display 200 can include a schematic of the bronchial passages or airways 100 where each site 150 is graphically identified. In the illustrated variation, each site is identified with a star. However, variations of the display can include making each site 150 separately identifiable for ease in correlating the score 202 with the actual location.

FIG. 2B also illustrates the display as showing the respective site 150 in table form with the grade or score 200 accompanying each site. Clearly, any variety of display modes is within the scope of the invention. For instance, the display may be coupled to a real-time virtual model of the airways so that a practitioner could identify the site as they navigate to the site with a bronchoscope or other treatment device. Such systems and devices to track a probe such as a catheter or endoscope through the body of a patient are discussed above.

In the example shown, sites B, B2, B3, B6, and B10 of the right lung, and B3-B10 of the left lobe received scores of 100. Although the illustrated display provides scores from 0 to 100, the principles of the algorithm can calculate scores in any scale. In addition, the scores are not limited to quantified values; they may be non-numeric rankings such as low, medium, high, etc.

The grades or scores 202 associated with each site 150 are calculated using a number of factors thought to increase the likelihood that the treatment locations allow trapped gasses to escape. The factors may also include safety considerations as well as whether a particular site is treatable due to the local anatomy.

Figure 3A:
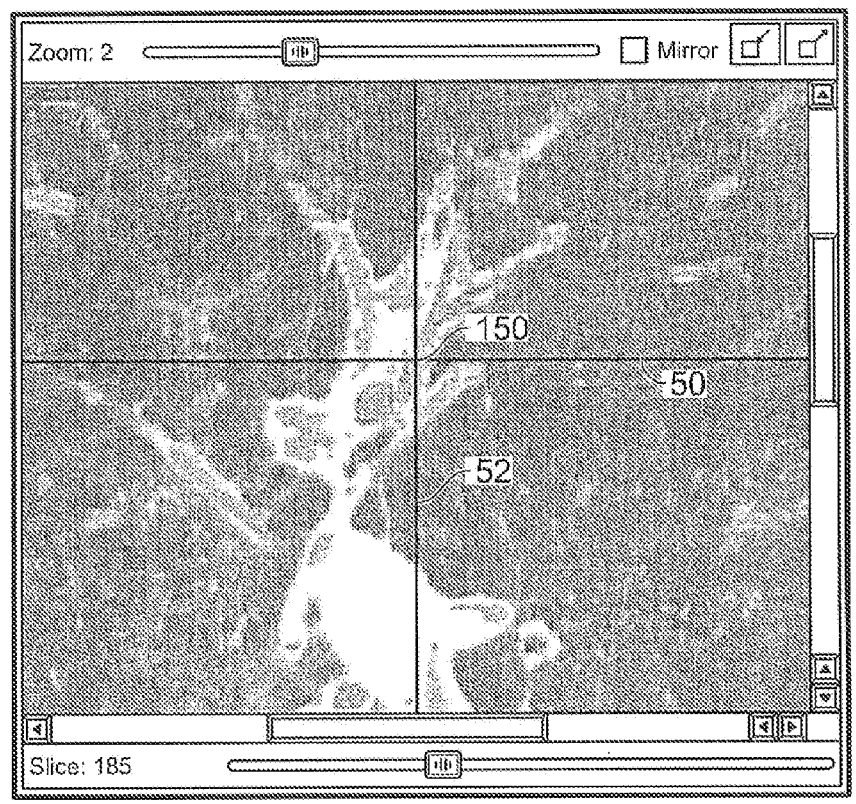
FIG. 3A-3C represents images from a CT scan identifying the site as well as other anatomic features, where such images may also be provided in the display of information given to the medical practitioner.
Figure 3B:
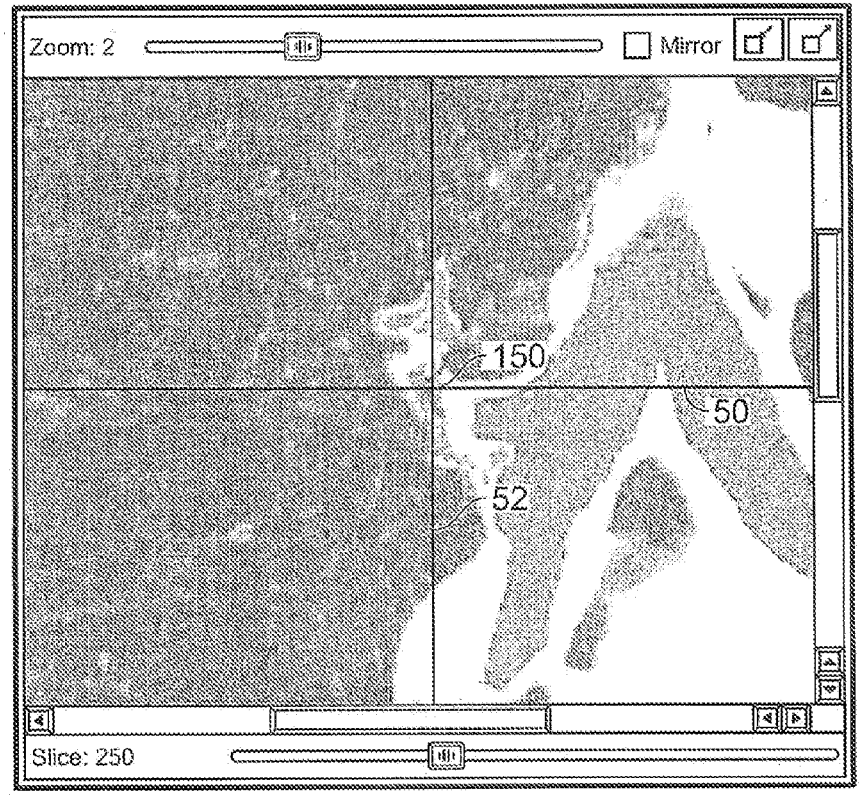
Figure 3C:
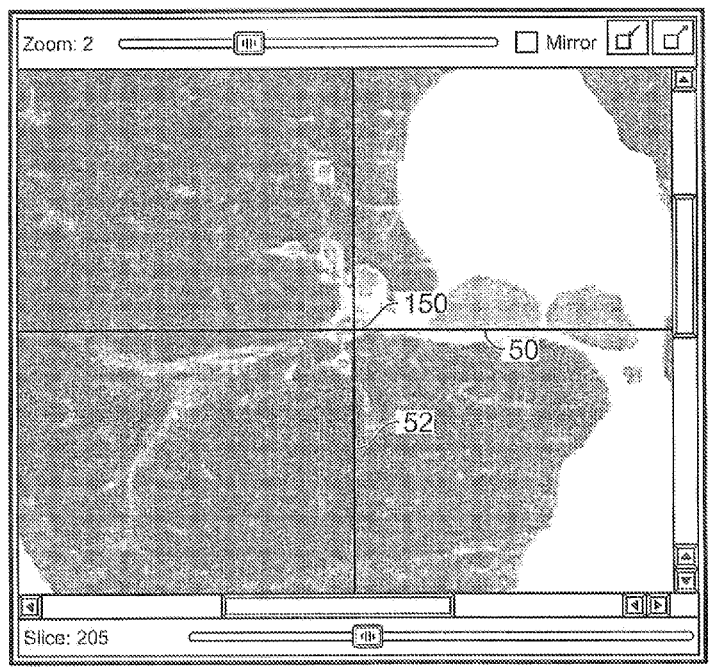

FIG. 3C illustrates a flowchart of one variation of a process 210 to assess treatment sites under the present invention. The flowchart provided is intended to illustrate one possible example of a process for assessing treatments sites. As discussed below, additional criteria can be used to calculate a score for a particular site. However, at a general level, the process includes pre-selection of the sites as noted above and using a number of factors based on the anatomy surrounding the site or the state of the disease to assess or score the site. Such anatomic factors include, but are not limited to airway size, airway wall thickness, amount of tissue destruction, uniformity of tissue destruction, amount of trapped gas retained in the region of the lung, proximity of the site to the destruction, the presence or absence of blood vessels, obstruction between the site and the region of trapped gas, other safety considerations (such as the presence of fissures, the pleura, mediastinum, neighboring airways, etc.)

Figure 2C:
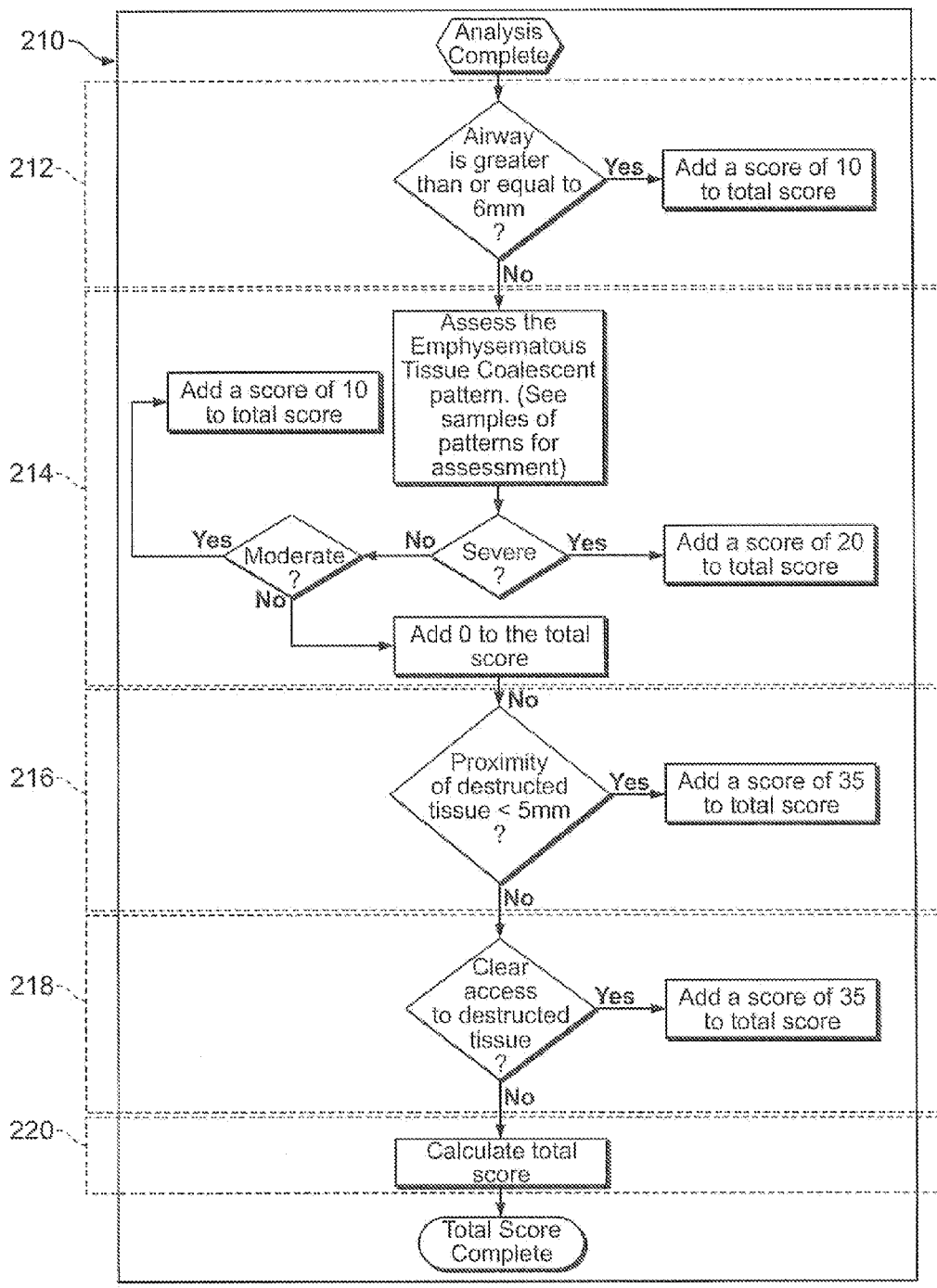
FIG. 2C represents one variation of a flow-chart documenting the process used to calculate a score for each site.

Turning now to FIG. 2C, the process 210 begins with the examination of the lung to accumulate the necessary data for evaluation within the procedure. In the example shown, the first decision and action steps 212 adjust the score of a particular site depending on an anatomic feature of the site itself. In the example, the score for a site is increased if the airway diameter is greater than or equal to a predetermined value (in this case a diameter of 6 mm or greater adds 10 to the score). These values are for illustration purposes only. Clearly, the invention is not limited to these values (10 points of greater or equal to 6 mm). Instead, any number of values may be used. In the example provided, the airway size of 6 mm is selected due to practical considerations when considering the size of a typical bronchoscope used to perform the procedure. Clearly, use of a smaller device could lower the desired airway diameter or adjust the score accordingly to increase the score for the ideal diameter. Moreover, the score itself can be altered for any number of reasons. For example, a medical practitioner may decide to give more or less weight to a particular size of the airway than in the sample process shown. In such a case, the practitioner could increase or decrease the score accordingly.

The next set of decisions 214 involves assessing a degree of one or more regions of lung tissue in the areas adjacent to the airways. As shown, a rating of severe destruction adds a score of 20, and a rating of moderate destruction adds a score of 10, If the site is neither moderate not severe, then no points are added to the score for that particular site. Again, although the sample process shows a decision process depending on severity of destruction only, other factors can be incorporated. For example, the method can evaluate the severity of the diseased tissue as well as the amount of trapped gas in the lobe of the lung containing the site.

Next, the analysis 216 assess whether the site is within a pre-determined distance from the diseased area of the lung. If the condition is net, a value is added to the score. Again, many variations are intended to be within the scope of the method. For example, instead of a binary decision, the assessment can provide weighted increments to the score for a particular site depending on the site's proximity to the diseased tissue. Moreover, a medical practitioner may wish to place more or less weight on the proximity of a larger site to destroyed tissue.

The decision of 218 shows an additional step evaluating an anatomic characteristic of the site. In this case, the anatomic characteristic is whether there is clear access to destroyed or diseased tissue. If the path is clear, then the score for that site is increased by a pre-determined value.

Finally, the process calculates the total score 220. These sets of steps are then repeated for each site. Ultimately, the results of the analysis are provided in a graphical form such as that shown in FIG. 2B. As discussed herein, the data may be produced in any number of formats. For example, when the steps of the method are incorporated into a virtual bronchoscopy type system, the results of the data can be superimposed upon the virtual rendering of the airways. In addition, the steps and calculations described herein can either be performed manually or automated via software.

During the procedure of creating extra-anatomic passages and/or placing implants in the airways, the medical practitioner must also be careful to avoid inadvertently perforating blood vessels, creating an opening in the pleural membrane, or causing other harm to the patient. Such features may also have a bearing on the after-effects of the procedure. For example, airway thickness is thought to have a direct relationship with the healing response at the site. Therefore, it may be desirable to consider the thickness of the airway wall at a site when assessing the site for the procedure.

Accordingly, variations of the methods described herein include using anatomic characteristics to reduce the chance of causing such harm or to reduce collateral effects of the procedure. For example, in determining the anatomic characteristics of the patient, the analysis can include identifying the location of blood vessels, the pleura, tumors, thickness of the airway wall or other anatomic features. Calculation of the score can then include weighting each site after taking these factors into consideration. Alternatively, or in addition, the characteristics can be used to provide guidance to the medical practitioner. For example, the presence or absence of blood vessels, or airway thickness can merely be reported to the practitioner without affecting the score. With the benefit of this information, the medical practitioner is better informed on how to treat the particular site.

FIGS. 2D to 2G illustrate samples of grading summaries for each site. As shown in FIGS. 2D and 2E, the output can include a breakdown of each site in a column with the respective score or item of information in the rows beneath the sire, FIGS. 2F and 2G illustrate additional data that can be provided to the medical practitioner. As noted, the data includes instructions that, while not used to calculate the grade or score, can be useful to the medical practitioner in locating the site and minimizing risks. In the illustrated example, the data provides the practitioner with a recommended location, access direction, and locations of any blood vessels, along with the severity of the disease, and score or grade.

Determination of anatomic characteristics.

As noted above, initial identification or selection of the patient can occur through various inclusion or exclusion criteria. Then the sites are identified, either being selected by the practitioner or by a standard procedure as noted above. Next, the degree of discussed anatomic features need to be identified as input data in order for carrying out the decisions and calculations of the score/grade. To accomplish this, the patient must undergo examination or imaging for creation of the input data. As noted above, one example of such imaging involves the use of CT scans. In one example, the patient undergoes a pre-treatment scan. Standard analysis of these scans is performed to identify the anatomic features for input data. In one example, the CT scan technique involves volumetric spiral scans through the entire chest at full inspiration and full expiration. Naturally, the methods and procedures of obtaining a proper CT scan will depend upon the type of equipment being used. In any case, the CT scan should allow identification of the various anatomic characteristics described herein.

FIGS. 3A to 3C show examples of CT scans used to determine the anatomic characteristics. In the figures, the target site 150 is represented by the convergence of the axis 50 and 52. The scans are analyzed, either manually or using software, using standard techniques to identify blood vessels, lung tissue, the pleura as well as additional anatomic features. These scans can also be included in the output along with the score/grade or other information provided to the medical practitioner prior to or during treatment.

Figure 3D:
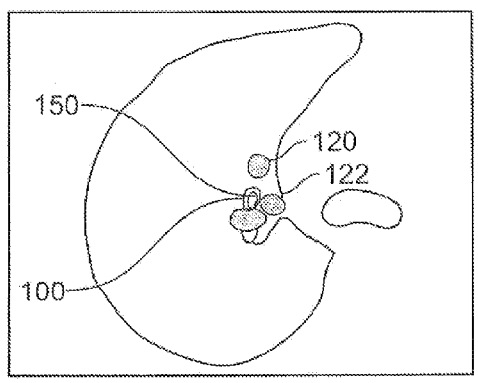
FIGS. 3D-3E represents analysis of the CT scans to produce the data used in assessing each site.
Figure 3E:
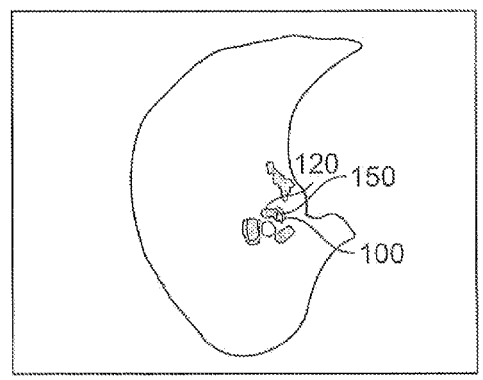

FIGS. 3D and 3E represent schematics of CT scans in which blood vessels 120, 122 as well as the airway 100 and site 150 are identified. Again, the data used in calculating a score for each site is obtained via analysis of such scans. For example, measurements can be obtained regarding the diameter of the vessels 120, 122, and the proximity of the vessels to the airway 100 and site 150. In addition, the airway diameter as well as airway thickness and distance to adjacent airways can be obtained.

Naturally, the techniques used to measure the anatomic features of the lung should be repeated consistently to avoid uncertainty. Accordingly, any number of techniques to measure airway diameter can be used in the methods described herein so long as the methods are consistent. As with any other measurement technique, the process may be iterative to identify an optimal technique. Currently, the airway measurement technique utilizes 30% of the center of the segmental airway to calculate the average of the diameter and wall thickness of the airway. Since airway shape is typically non-circular, the major and minor diameters are calculated.

The airway wall diameter and thickness can be determined by measuring the apical bronchus section of images obtained from CT study. The technique involve casting a ray outward from the central axis of the airway to the airway wall and parenchyma and applying the "full-width at half-maximum" principle (a method for characterizing the width of a peak on a graph).

Airway diameter may be important for clinical effects as well as to acknowledge device limitations. For example, it may be found that airways having a minimum diameter demonstrate improved effectiveness for releasing trapped gas. Accordingly, airways greater than that minimum diameter would be identified as a target region.

As noted above, physical device considerations may limit the ability to treat certain regions in the airways. In one example, due to the size requirements of some devices, treatment is limited to airways having a size that allows for maneuverability and articulation of the device. Presently, the diameter size of the typical bronchoscope is 5 mm; hence, the desired minimum size of the airways is greater than 6 mm. However such a size limit may be changed as the device configuration changes.

Another constraint is the length of the devices. The common length of standard bronchoscopes limits treatment to within 24 inches from the mouth. Accordingly, the CT scans can be used to determine the length required to access that particular site and factor this into the calculation of the grade or score.

With regard to the assessment of whether a blood vessel might pose a problem with a particular site; a number of parameters can be used. For example, the data analysis can determine existence of blood vessel in the vicinity of each location. Next, any blood vessels with a predetermined radius and of a predetermined diameter can be noted. For example, one variation of the procedure noted blood vessels 1 mm or larger within a 1 cm radius of the site. Alternatively, the method may include counting the number of vessels or determining a "vessel free" space at a particular site.

Again, anatomic characteristics according to the present method may include airway diameter, distance from the mouth, the articulation angles required to reach the particular region, intraparenchymal margin, and the exterior perimeter of the parenchymal margin. The anatomic characteristics/parameters may be selected based on numerous criteria. In another example, target regions in the airway that are securely within the intraparenchymal margin may be selected to minimize the risk that the implant or procedure causes harm to the patient.

In addition, the anatomic criteria may be somewhat related to physical parameters of the treatment system. For example, surgical systems designed to make extra-anatomic passages and place implants therein currently include a number of components. Such components may include an access device such as a bronchoscope, and treatment devices such as a Doppler device, a holemaking device, an implant delivery device, etc.

The following examples illustrate the potential relationship between physical parameters of he system and anatomic parameters. In order to screen potential target sites, the limitations of the system components such as size, length, and bending radius are identified. Accordingly, if given these parameters, it is impossible to reach certain target regions in the airways, then these unreachable regions may be eliminated as potential target sites. For example, if a bronchoscope can only articulate to a certain degree, then those regions in the lungs that would require excessive bending of the bronchoscope could be eliminated. In another example, the distance between the target region and the mouth may be important based upon physical parameters of the treatment system being used (i.e., the treatment system must be able to reach the airway site).

Once the reachable target regions are identified, the criteria discussed above may be combined with assessments of regions with excessive destruction of tissue, higher ratios of trapped gas, fewer surrounding blood vessels, dense tissue, excessive collateral ventilation, and/or nay other criteria discussed herein.

Assessing the disease state of the lung.

As with determining the anatomic characteristics of the site and surrounding tissue. Assessment of the diseased regions of the lung as well as the degree of the diseased region should be made with consistency. For example, is important that a "region" is defined consistently as the region will directly affect the calculation of volume of trapped gas. Additionally, definition of a region shall take into account the clustering of emphysematous tissues.

Figure 4A:
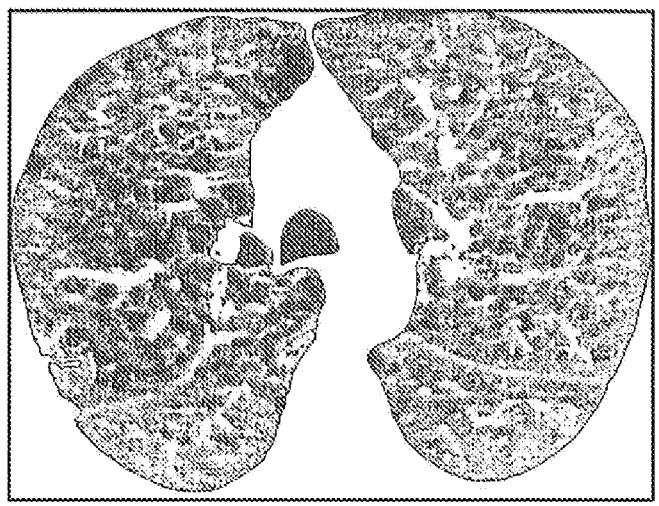
FIGS. 4A-4C represent samples of severe, moderate, and mild coalescent patterns of emphysematous lung tissue used to compare to lung tissue being assessed in order to rate the degree of diseased tissue.
Figure 4B:
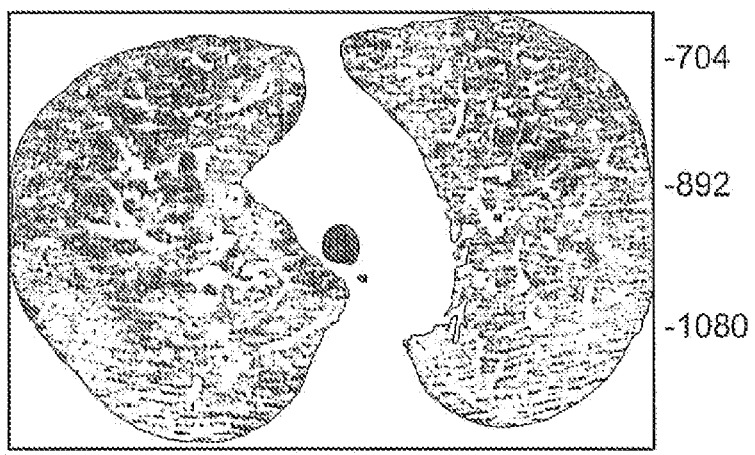
Figure 4C:
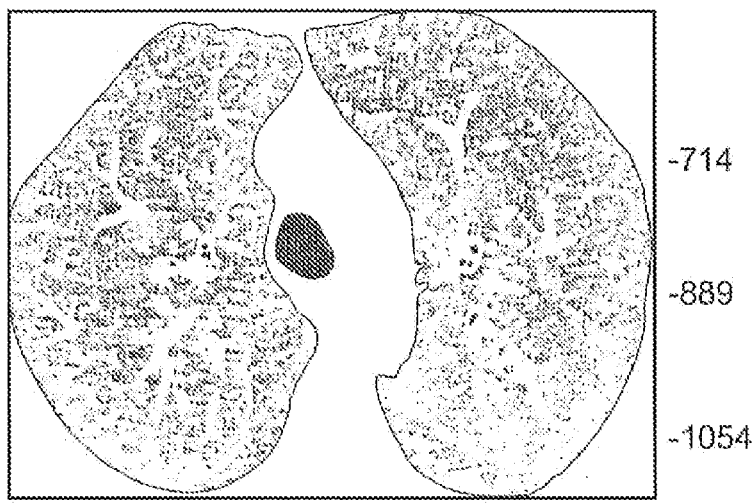

In one example, assessment of diseased regions of tissue can be made against a database of images with diseased patterns. Therefore, the baseline reference for diseased lung pattern remains consistent for each disease region in the lungs. For example, FIGS. 3D to 3F illustrate samples of respective severe, moderate, and mild coalescent patterns of emphysematous tissue. Comparison of these samples, either by manual comparison, or the use of software, allows for categorizing of the severity of diseased region within the patients lungs. In the present example, the variation between the coalescent patterns of FIGS. 4A to 4C is apparent in the shade of the pattern as well as the amount of "black holes" in the image, which represents trapped gas or destructed tissue.

Methods to assess diseased regions of the lungs can also, or alternatively, involve quantitative analysis of high resolution CT scans. In one example such quantitative analysis focuses on the changes in lung density as a function of lung volume.

The following calculation is used to determine the distribution of emphysema including size and severity of the diseased tissue. Lung density (D)=lung weight divided by the sum of the volume of gas in the lung (V) plus tissue and blood volume. Coxson H O, Rogers R M, Whittall K P, D'Yachkova Y, Paré P D, Sciurba F C, Hogg J C. *A quantification of the lung surface area in emphysema using computed tomography*. Am J Respir Crit Care Med 1999;159:851-856, teach that density of gas-free lung tissue and blood is very close to 1, lung weight in gm very nearly equals lung tissue and blood volume (in cc). Accordingly, for purposes of the calculation, these values are assumed to be constant (k) and independent of V. Therefore: $D=k/(k+V)$. In this equation D is inversely proportional to k+V, and the relationship between the two will be hyperbolic. The inverse equation: $1/D=(k+V)/k=1+V/k$ is the equation of a straight line with an intercept of 1 and a slope of 1/k. The technical term for the inverse of density; is specific volume, $SV=1/D=1+V/k$ (equation 1). When the lungs are gas-free and V=0, SV=1. This gives us 1 point on a graph of SV vs V. A single other point will define the whole line which is the locus of all points defining SV at any value of V. Complete HRCT scans measure k+V at the lung volume at which the scan was made. The scans also make reasonable estimates of k. Thus a single HRCT scan can be used to define the complete relationship between SV and V.

In normal lungs we predict that this distribution will be narrow and that the values of SVr will be relatively homogeneous. We also predict that the between individual variability in SV will be small. It is evident from equation 1 that the between individual variability is determined by the between individual variability of V/k. If V is the taken as its value at TLC, then individuals with large TLC's usually have the biggest (weightiest) lungs and vice versa. If so, then at any lung volume less than TLC expressed as %TLC, the variability of V/k between individuals should be small at all values of V.

In emphysematous lungs areas of gas trapping will be identified as regions whose SVr changes little if at all with V, so that the change ($\Delta$) in SVr will be much less than the average; i.e., $\Delta SVr<<\Delta SV$. In homogeneous emphysema we predict that the distribution of slopes will be bimodal with emphysematous lung regions having a low values of $\Delta SVr/\Delta V$ with a narrow range of these low values, and other remaining normal regions with high values of $\Delta SVr/\Delta V$ and a narrow range of these values as well. Thus the lung could be considered as a two compartment system, one with emphysema and the other remaining close to normal. Other cases of emphysema might have a continuous distribution of $\Delta SVr/\Delta V$ slopes ranging from very low to very high. If so, the distribution of these values should carry information about the distribution of emphysema throughout the lungs.

A Density Mask is another variation used to determine the degree of destruction within each lobe. Density Mask is a commonly used algorithm to quantify the amount of emphysematous region. The Density Mask algorithm calculates the number of pixels with density values of less than certain pre-defined number. (Typically −910 Hounsfield Units). The total area of emphysematous pixels provides the calculated percentage of lung destruction. The percentage of destruction is further used to define the "CT score" of each lobe, which represents the degree of deterioration of alveolar walls in the same regions of the lungs.

The "density mask" can be a primary measure to assess the trapped gas volume in each lobe. To compute the % volume difference in each requires computing the lobar volume from the TLC (total lung capacity) scan by summing the volumes of all voxels included in the lobe. The lobar volumes are also computed at RV (residual volume). The percentage of lobar volume RV over TLC determines a value for quantifying the amount of trapped gas.

Additional variations of the invention include algorithms to create road-maps or treatment plans for use with the scoring/grading of each respective site. Such example include:

EXAMPLE 1

1. Identify the treatable regions of the 18 segmental segments in the 5 lobes of the lung for:
 1.1 Airway diameter distance from mouth, articulation angles, and intraparenchymal margin to determine bronchoscopic access and treatable surfaces;
2. Once the treatable regions are identified, evaluate the vessel free locations by:
 2.1 Tracking the branches of the pulmonary arteries and veins from the 2 arterial and 2 venous vessels entering and exiting the lung, then
 2.2 Identifying locations within the treatable regions with sufficient distance from the pulmonary branches
3. Once the vessel free locations within the treatable regions are identified, evaluate the access to trapped gas by:
 3.1. Determining the accessible parenchymal tissue density within local and regional volumes
 3.2. Ranking the treatment locations by local and regional tissue density
4. Creating a site road may to indicate to the bronchoscopist the preferred treatment locations.

EXAMPLE 2

1. Identify the regions of trapped gas, by:
 1.1. Determining the local and regional parenchymal tissue densities throughout the lung
 1.2. Rank ordering the regions
2. Evaluating transbronchial access paths to the trapped gas or collaterally ventilated regions by;
 2.1. Identifying the segmental airways communicating with the regions, and
 2.2. Determining bronchoscopic access and the treatable regions within these segments.
3. Identifying the blood vessel free locations, by
 3.1. Tracking the branches of the pulmonary arteries and veins from the 2 arterial and 2 venous vessels entering and exiting the lung, then
 3.2. Identifying locations within the treatable regions with sufficient distance from the pulmonary branches
4. Creating a site road map to indicate to the bronchoscopist the preferred treatment locations.

The invention herein it described by examples and a desired way of practicing the invention is described. However, the invention as described herein is not limited to that specific description in any manner. Equivalence to the description as hereinafter described is considered to be within the scope of protection of this patent.

The above methods and algorithms may be incorporated in any computer-assisted display or visualization system as described above.

Also, the following applications contain methods and/or devices that may be combined with the above principles:

What is claimed is:

1. A method of assessing a plurality of treatment sites in airways of a hyperinflated lung of a patient, the method comprising:
 identifying the plurality of sites within the airways of the diseased lung;
 determining at least one anatomic characteristic of each site;
 assessing a degree of a plurality of diseased regions in the lung;
 calculating a score for each site based on the degree of the plurality of diseased regions in the lung, at least one anatomic characteristic of each site and a proximity of the site to at least one of the diseased regions; and
 displaying each score in association with each site in graphical form.

2. The method of claim 1, where identifying the plurality of sites comprises selecting at least one site per each segmental airway of the bronchi.

3. The method of claim 1, further comprises performing non-invasive imaging to assess the degree of the plurality of diseased regions of the lung and to determine at least one anatomic characteristic of each site.

4. The method of claim 3, where the non-invasive imaging is chosen from a group consisting of x-ray, ultrasound, Doppler, acoustic imaging, MRI, PET and CT.

5. The method of claim 3, where assessing the degree of the diseased region in the lung comprises comparing the diseased pattern in the region to a database of images with diseased pattern.

6. The method of claim 1, further comprises displaying information regarding at least one anatomic characteristic of the site when displaying the score of the site.

7. The method of claim 6, where displaying information regarding at least one anatomic characteristic comprises displaying information regarding the location or size of blood vessels.

8. The method of claim 6, where displaying information regarding at least one anatomic characteristic comprises displaying information regarding the location a pleura relative to the site.

9. The method of claim 1, where determining at least one anatomic characteristic of each site comprises identifying the location of the blood vessels within a distance from the site.

10. The method of claim 1, where calculating the score for each site comprises adjusting the score proportionally to the degree of the diseased region.

11. The method of claim 10, where calculating the score for each site further comprises increasing the score as the proximity of the site to one of the diseased regions decreases.

12. The method of claim 1, where determining at least one anatomic characteristic of each site comprises determining the size of airway diameter of each site.

13. The method of claim 12, where calculating the score for each site comprises increasing the score if the average airway diameter is greater than a pre-determined diameter.

14. The method of claim 1, where determining at least one anatomic characteristic of each site comprises determining an average airway thickness of each site.

15. The method of claim 14, where calculating the score for each site comprises increasing the score if the average airway thickness is within a pre-determined thickness range.

16. The method of claim 1, where determining at least one anatomic characteristic of each site comprises determining the distance from an anatomic reference point on the patient.

17. The method of claim 16, where the anatomic reference point comprises a carina of the airways.

18. The method of claim 16, where the anatomic reference point comprises a mouth of the patient.

19. The method of claim 1, further comprises examining paths between the site and at least one of the diseased regions for any obstruction.

20. The method of claim 19, where calculating the score for each site further comprises increasing the score if the path is free from obstructions on the path.

21. The method of claim 19, where the obstruction comprises an obstruction selected from the group consisting of one or more of the followings: blood vessels, adjacent airways, a fissure, a pleura, and a mediastinum.

22. The method of claim 1, where assessing a degree of a plurality of diseased regions in the lung comprises assessment of a degree of tissue destruction in the diseased region.

23. A method for identifying treatment sites in airways of a patient's lung for treatment by a surgical system comprising at least one component device, the method comprising:
    identifying at least one parameter of the component device;
    identifying a target region in the airway based on at least one or more anatomical parameters;
    locating at least one location of diseased lung tissue;
    selecting a plurality of treatment sites by assessing the anatomy between at least one of the potential treatment sites and at least one location of diseased lung tissue;
    displaying the plurality of treatment sites in data, electronic or graphic form.

24. The method of claim 23, where the component device comprises a plurality of component devices.

25. The method of claim 24, where the plurality of component devices comprises an access device and a treatment device.

26. The method of claim 25, where the access device comprises of a bronchoscope.

27. The method of claim 25, where the treatment device is selected from a group consisting of a holemaking device and an implant delivery device.

28. The method of claim 23, where the system parameter comprises a parameter selected from a group consisting of a length, diameter, and bending radius of one or more of the component devices.

29. The method of claim 23, where the anatomical parameters of the target region comprise a parameter selected from the group consisting of a diameter of the airway, a length of the airway between a mouth and the target region, an articulation angle between a parent and child airway in the path to the target region, a summation of the articulation angles, a length of the airway between the target region and an intraparenchymal margin of the lung, an indication of a blood vessel at the target region, a position of a blood vessel at the target region.

30. The method of claim 23, where identifying a target region in the airway based on one or more at least one or more anatomical parameters comprises using a non-invasive imaging mode selected form the group consisting of x-ray, ultrasound, Doppler, acoustic imaging, MRI, PET and CT.

31. The method of claim 23, where the region of diseased lung tissue comprises areas of hyperinflated lung tissue.

32. The method of claim 23, where the region of diseased lung tissue comprises areas of trapped gas within parenchymal tissue.

33. The method of claim 23, where selecting the plurality of treatment sites comprises ranking the potential treatment sites.

34. The method of claim 33, further comprising determining a plurality of potential treatment sties by comparing at least one of the anatomical parameters of the target region with at least one system parameter to assess the ability of the system to access the target region.

35. The method of claim 34, where identifying the target region comprises selecting the target region based on anatomical parameters comprising a maximum airway diameter, a minimum airway diameter, and a maximum airway length to the target region.

36. The method of claim 34, further comprising creating an extra-anatomic opening in an airway wall at the treatment site.

37. The method of claim 36 further comprising inserting an implant into the extra-anatomic opening.

38. A method of site selection for an airway bypass procedure in airways of a diseased lung using a surgical system, comprising:
    identifying treatment regions of the airway reachable by the surgical system;
    identifying diseased regions of the lung for treatment based on a severity of disease;
    creating a ranking of treatment sites by comparing the diseased regions with the treatment regions to determine whether a transbronchial access path exists; and
    providing an output of treatment sites in electronic, data, or graphic form.

39. The method of claim 38, where identifying diseased regions of the lung further includes identifying the regions of the lung for the presence of blood vessels.

40. The method of claim 38, where identifying diseased regions of the lung comprises determine the degree of destruction within each lobe of the lung.

41. The method of claim 38, where identifying diseased regions of the lung includes determining treatable areas within each lobe with most trapped gas.

42. The method of claim 38, where identifying diseased regions of the lung includes determining areas with dense collateral ventilation in the lung.

43. The method of claim 38, where identifying diseased regions of the lung include measuring pulmonary blood flow.

44. The method of claim 38, where identifying diseased regions of the lung include determining diameter and wall thickness of an airway.

* * * * *